United States Patent

Braun et al.

[11] Patent Number: 5,879,411
[45] Date of Patent: Mar. 9, 1999

[54] COMPOSITION AND METHOD FOR DYEING KERATIN FIBERS WITH O-BENZOQUINONES AND AMINO- OR HYDROXY-CONTAINING COMPOUNDS

[75] Inventors: Hans-Juergen Braun, Ueberstorf; Gisela Umbricht, Fribourg, both of Switzerland

[73] Assignee: Wella AG, Darmstadt, Germany

[21] Appl. No.: 991,933

[22] Filed: Dec. 16, 1997

[30] Foreign Application Priority Data

Dec. 20, 1996 [DE] Germany ............ 196 53 292.2

[51] Int. Cl.⁶ ................................. A61K 7/13
[52] U.S. Cl. ................. 8/405; 8/589; 8/590; 8/603; 8/662
[58] Field of Search ................. 8/405, 406, 407, 8/408, 409, 410, 414, 415, 662, 589, 590, 603

[56] References Cited

U.S. PATENT DOCUMENTS

| 4,750,908 | 6/1988 | Rosenbaum et al. ............ 8/429 |
| 4,867,751 | 9/1989 | Lang et al. ............ 8/405 |
| 5,053,053 | 10/1991 | DeLabbey et al. ............ 8/423 |
| 5,064,442 | 11/1991 | Grollier ............ 8/407 |
| 5,178,637 | 1/1993 | Lagrange et al. ............ 8/405 |
| 5,259,849 | 11/1993 | Grollier et al. ............ 8/405 |
| 5,427,588 | 6/1995 | Lagrange et al. ............ 8/423 |

FOREIGN PATENT DOCUMENTS

| 0 376 776 A2 | 7/1990 | European Pat. Off. . |
| 43 18 742 A1 | 12/1994 | Germany . |
| 691 03 962 T2 | 2/1995 | Germany . |
| 43 35 625 A1 | 4/1995 | Germany . |
| 43 35 626 A1 | 4/1995 | Germany . |
| 43 35 624 A1 | 6/1995 | Germany . |
| 44 34 494 A1 | 3/1996 | Germany . |

*Primary Examiner*—Paul Lieberman
*Assistant Examiner*—Caroline D. Liott
*Attorney, Agent, or Firm*—Michael J. Striker

[57] ABSTRACT

A non-oxidative dye composition for keratin fibers contains an o-benzoquinone compound of formula (I):

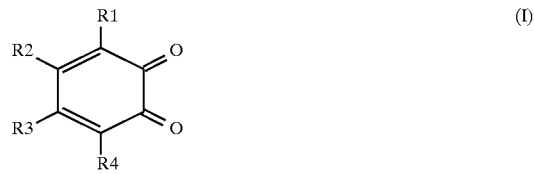

wherein R1, R2, R3 and R4 are each, independently of each other, hydrogen, chlorine, an alkyl group with from 1 to 5 carbon atoms, an alkoxy group with from 1 to 5 carbon atoms, an alkylenedioxy group with from 1 to 2 carbon atoms or an amino group —$NR^5R^6$, wherein $R^5$ and $R^6$ are each, independently of each other, hydrogen, an alkyl group having from 1 to 6 carbon atoms or an aryl group; and at least one amino- or hydroxy-compound of formula (II), X—A—Y, wherein X represents a nitro group, a cyano group or a sulfonate group; Y represents a hydroxy group or an amino group —$NR^aR^b$, wherein $R^a$ and $R^b$ are each, independently of each other, hydrogen or an alkyl group having 1 to 4 carbon atoms, and A represents a substituted or unsubstituted straight chain, cyclic or branched alkyl group having from 1 to 6 carbon atoms or a substituted or unsubstituted aromatic, heterocyclic or carbocyclic group.

11 Claims, No Drawings

COMPOSITION AND METHOD FOR DYEING KERATIN FIBERS WITH O-BENZOQUINONES AND AMINO- OR HYDROXY-CONTAINING COMPOUNDS

BACKGROUND OF THE INVENTION

The present invention relates to a composition for dyeing keratin fibers which contains o-benzoquinone in combination with certain amino or hydroxy compound, as well as a method for dyeing keratin fibers using this composition.

Generally direct-dyeing dye compounds or oxidation dyestuffs which arise by oxidative coupling of one or more developer substances together with one or more coupler substances are used for dyeing of keratin-containing fibers, for example hair, wool or fur. Intense dyeing with good fastness properties may of course be obtained with oxidation dyestuffs which develop the color, however strong oxidizing agents, such as hydrogen peroxide, which are used frequently cause damage to the fibers. Direct-dyeing hair dyes are applied under safer conditions, but have the disadvantage that they have unsatisfactory fastness properties.

According to German Patent Application DE-OS 43 35 624 dye compositions based on p-benzoquinone, which avoid the use of an additional oxidizing agent, provide an alternative here.

The dyeing process described in German Patent Application DE-OS 43 35 624 is however difficult to perform in practice, since the dye mixture must be heated prior to use to its boiling temperature and subsequently filtered and frequently leads to unsatisfactory dyeing results.

SUMMARY OF THE INVENTION

It is an object of the present invention to provide a non-oxidative dye composition for dyeing keratin fibers which is easy to use and provides intense colors on the dyed fibers.

It has now been found that a composition for dyeing keratin fibers, such as human hair, wool or fur, which contains (a) o-benzoquinone compounds and (b) certain amino- and hydroxy-compounds, which are substituted with strongly electron withdrawing substituents, satisfies this object in an outstanding manner.

According to the invention the composition for dyeing keratin fibers, especially human hair, contains an o-benzoquinone compound of formula (I):

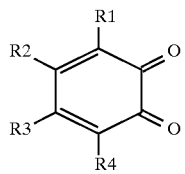
(I)

wherein R1, R2, R3 and R4 are each, independently of each other, hydrogen, chlorine, an alkyl group with from 1 to 5 carbon atoms, an alkoxy group with from 1 to 5 carbon atoms, an alkylenedioxy group with from 1 to 2 carbon atoms or an amino group —$NR^5R^6$, wherein $R^5$ and $R^6$ are each, independently of each other, hydrogen, an alkyl group having from 1 to 6 carbon atoms or an aryl group, and at least one amino- or hydroxy- compound of formula (II)

X—A—Y (II), wherein X represents a nitro group, a cyano group or a sulfonate group, Y represents a hydroxy group or an amino group —$NR^aR^b$, wherein $R^a$ and $R^b$ are each, independently of each other, hydrogen or an alkyl group having 1 to 4 carbon atoms, and A represents a substituted or unsubstituted straight chain, cyclic or branched alkyl group having from 1 to 6 carbon atoms or a substituted or unsubstituted aromatic, heterocyclic or carbocyclic group.

Preferably the compounds of the formula II used in the dye composition according to the invention include 1) aniline derivative compounds of the formula (IIa):

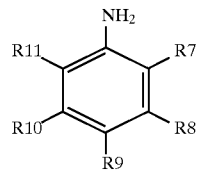
(IIa)

in which at least one of the groups R7, R8, R9, R10 and R11 represent a nitro group, a cyano group or a sulfonate group, and the remaining groups R7 to R11, independently of each other, are each hydrogen, chlorine, a hydroxy group, an amino group, an alkyl group having from 1 to 5 carbon atoms, a hydroxyalkyl group having from 1 to 5 carbon atoms, an alkoxy group having from 1 to 5 carbon atoms, a hydroxyalkoxy group having from 2 to 5 carbon atoms or a carboxyl group;

2) phenol derivative compounds of the formula (IIb)

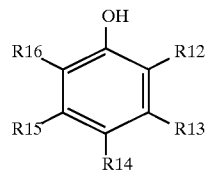
(IIb)

wherein at least one of the groups R12, R13, R14, R15 and R16 represents a nitro group, a cyano group or a sulfonate group, and the remaining groups R12 to R16, independently of each other, represent a hydrogen, chlorine, a hydroxy group, a hydroxyalkyl group having from 1 to 5 carbon atoms, an alkoxy group having from 1 to 5 carbon atoms, a hydroxyalkoxy group having from 2 to 5 carbon atoms or a carboxyl group;

3) multicenter aromatic isocyclic compounds, which are substituted with at least one amino or hydroxy group and at least one nitro group, cyano group or sulfonate group;

4) five to six-membered heterocyclic compounds with 1 to 3 nitrogen atoms, which are substituted with at least one amino or hydroxy group and at least one nitro group, cyano group or sulfonate group; and/or 5) open-chain saturated or unsaturated compounds which have at least two amino groups or each have an amino group and a hydroxy group and at least one nitro group, cyano group or sulfonate group.

The above-named compounds can also be present in the form of their physiologically compatible acid-addition compounds, for example in the form of the chloride, sulfate or lactate, and/or in phenols or carboxylates in the form of their alkali salts, alkaline earth salts or their quaternary ammonium salts.

Particularly preferred compounds of the formula (II) include 2-nitroaniline, 3-nitroaniline, 4-nitro-o-phenylenediamine, 2-amino-5-nitrophenol, 1,4-diamino-2-nitrobenzene, 2-amino-3,5-dinitrophenol, picramic acid, 1,2-diamino-3-nitrobenzene, 2-cyanoaniline, diaminomaleic acid dinitrile, 1-amino-2-naphthol-4-sulfonic acid, 2-aminophenol-4-sulfonic acid, 2-(4,5,6-trihydroxy-3-oxo-3H-xanthen-9-yl)-benzene sulfonic acid (pyrogallol red) and p-phenylenediamine sulfonic acid.

Suitable o-benzoquinone compounds of formula I include, for example 4,5-dimethoxy-1,2-benzoquinone, 4,5-methylenedioxy-1,2-benzoquinone, 4,5-dianilino-1,2-benzoquinone, o-chloranile and 3,5-di-(tert-butyl)-1,2-benzoquinone.

The o-benzoquinone of formula (I) is contained in the dye composition according to the invention in an amount of 0.02 to 3 percent by weight, especially in an amount of 0.03 to 1 percent by weight, while the compound of formula (II) is used in an amount of 0.03 to 6 percent by weight, especially in an amount of 0.03 to 1 percent by weight.

The form of the preparations of the hair dye composition according to the invention can, for example, be a solution, especially an aqueous or aqueous-alcoholic solution. Preferred forms of these preparations include those of a cream, of a gel, of an emulsion or those of a surfactant-containing foam composition, for example a shampoo.

The pH value of the dye composition is in a range of 3 to 10.5, especially at a pH of 4 to 9. The adjustment of the alkaline pH values can be performed with ammonia or with organic amines, such as monoethanol amines or triethanolamines, while organic acids, such as lactic acid, citric acid or acetic acid, can be used for adjusting acid pH values.

Understandably the above-described hair dye composition can include conventional additive ingredients commonly used in hair dye compositions, as needed, for example preservatives and perfume oils; solvents, such as water, lower aliphatic alcohols, for example ethanol, propanol and isopropanol, or glycols, such as glycerol and 1,2-propylene glycol; wetting agents or emulsifiers from the classes of anionic, cationic, amphoteric or nonionic surfactants, such as fatty alcohol sulfates, ethoxylated fatty alcohol sulfates, alkyl sulfonates, alkylbenzene sulfonates, alkyltrimethylammonium salts, alkylbetaines, ethoxylated fatty alcohols, ethoxylated nonylphenols, fatty acid alkanol amides, ethoxylated fatty acid esters; thickeners, such as higher fatty alcohols, starches or cellulose derivative compounds, softening agents, petrolatum (Vaseline®), paraffin oil, fatty acids; and care materials, such as cationic resin, lanolin derivative compounds, cholesterol, vitamins, pantothic acid and betaine. The above-mentioned ingredients are used in amounts common for their purposes, for example the wetting agents and emulsifiers are used, for example, in concentrations of 0.5 to 30 percent by weight, the thickeners in an amount of from 0.1 to 25 percent by weight and the care materials in a concentration of 0.1 to 5.0 percent by weight.

Both compounds of formula (I) and (II) can be packaged separately or together in a water-free form or in a form of a ready-to-use formulation.

Preferably both compounds of formula (I) and (II) however are packaged separately in the form of a 2-component pack, in which both components can be present in water-free form and also in the form of an aqueous or aqueous-alcoholic preparation. In so far as both components are present in water-free form, they are dissolved prior to use in water or a suitable aqueous or aqueous-alcoholic cosmetic base, in which both components can be present in separate solutions or in a common solution.

For dyeing hair the dye composition according to the invention is applied to the hair in an amount sufficient for the hair dyeing, allowed to act there for about 20 to 30 minutes at a temperature of about 20° to 40° C., and subsequently rinsed with water or with a commerical hair shampoo. Subsequently the hair is dried.

In the embodiments in which the composition according to the invention is in the form of a 2-component package, it is possible to mix the compound of formula (I) and the compound of formula (II), either directly with each other immediately prior to use and to apply the obtained preparation to the hair, or however to apply both compounds of formula (I) and (II) one after the other to the hair, wherein about a time interval of from about 2 to 5 minutes can elapse between the application of the compound of formula (I) and the application of the compound of formula (II).

The dye composition according to the invention allows a simple and intense coloring or dyeing of keratin fibers, especially human hair, with an outstanding stability against action of light and shampooing.

The hair dye composition according to the invention can produce a plurality of color shades, for example yellow, orange, brown, red, violet or black dye tones.

The following examples should illustrate the subject matter of the invention in more detail, without limiting it.

EXAMPLES

Examples 1 to 13: Hair Dye Composition

In all examples dye solutions of the following compositions are used:

Dye Solution (I)

Y● 2.5 mmol o-benzoquinone of formula (I)

10.0 g lauryl alcohol diglycolether sulfate sodium salt (28% aqueous solution)

10.0 g isopropanol ad 100.0 g water, desalenated

Dye Solution (II)

Z● 2.5 mmol compound of formula (II)

10.0 g lauryl alcohol diglycolether sulfate sodium salt (28% aqueous solution)

10.0 g isopropanol ad 100.0 g water, desalenated

The factors Y and Z correspond to the proportions disclosed in the following Table 1 for each of the 13 examples.

The adjustment to the desired acid pH-value occurs by addition of 10 grams of lactic acid.

The dye solution (I) is applied to the hair to be died uniformly at room temperature (20° to 25° C.). After an acting time of 5 minutes the dye solution (II) (as well as a 10% lactic acid solution as needed) is applied evenly to the hair.

After a further acting time of 20 minutes at 40° C. the hair is rinsed with lukewarm water and dried.

The dyeing results obtained with different dye solutions are tabulated in the following Table I.

The L,a and b color measured values measured for the present examples were determined with a calorimeter of the Minolta Firm, Type Chromameter II.

The L-value is a measure of the brightness (the less the L-value, the greater the dyed color intensity), while the a-value is a measure of the red component (the greater the a value, the greater the red component). The b-value is a measure of the blue component of the color (the greater the blue component, the more negative is the b-value).

TABLE 1

COLOR PROPERTIES OF HAIR DYED WITH THE
DYE COMPOSITIONS OF THE INVENTION USING 4,5-DIMETHOXY-
1,2-BENZOQUINONE AS THE o-BENZOQUINONE OF FORMULA I

| Example | Compound of Formula II | Ratio Y:Z* | Added Acid | Color | L | a | b |
|---|---|---|---|---|---|---|---|
| 1a | 4-nitro-o-phenylene-diamine | 1:4 | none | orange-brown | 50.9 | 30.7 | 44.8 |
| 1b | 4-nitro-o-phenylene-diamine | 1:4 | lactic | orange-brown | 42.3 | 29.7 | 36.9 |
| 1c | 4-nitro-o-phenylene-diamine | 2:1 | none | orange | 50.2 | 30.7 | 42.3 |
| 1d | 4-nitro-o-phenylene-diamine | 2:1 | lactic | orange-brown | 37.9 | 28.0 | 23.8 |
| 2a | 2-amino-5-nitrophenol | 1:4 | none | yellow-bright brown | 55.2 | 19.2 | 59.1 |
| 2b | " | 1:4 | lactic | brown with yellow tones | 34.2 | 12.1 | 24.1 |
| 2c | " | 2:1 | none | rose red | 42.4 | 29.7 | 37.0 |
| 2d | " | 2:1 | lactic | rose red | 28.0 | 21.9 | 15.8 |
| 3a | 1,4-diamino-2-nitro-benzene | 1:2 | none | red-brown | 33.4 | 31.1 | 16.8 |
| 3b | 1,4-diamino-2-nitro-benzene | 1:2 | lactic | brown | 29.9 | 17.4 | 12.5 |
| 4a | 2-nitroaniline | 1:2 | none | orange | 58.3 | 30.1 | 59.6 |
| 4b | " | 1:2 | lactic | orange | 58.4 | 17.5 | 56.1 |
| 5a | 2-amino-3,5-dinitro-phenol | 1:2 | none | orange | 47.9 | 38.9 | 47.1 |
| 5b | 2-amino-3,5-dinitro-phenol | 1:2 | lactic | orange | 55.6 | 23.8 | 56.8 |
| 6a | picramic acid | 1:2 | none | reddish brown | 32.5 | 31.9 | 23.9 |
| 6b | " | 1:2 | lactic | dark brown | 19.1 | 10.9 | 3.5 |
| 7a | 1,2-diamino-3-nitro-benzene | 1:2 | none | copper | 37.8 | 36.1 | 30.1 |
| 7b | 1,2-diamino-3-nitro-benzene | 1:2 | lactic | copper-brown | 34.4 | 22.0 | 21.9 |
| 7c | 1,2-diamino-3-nitro-benzene | 2:1 | none | copper | 40.2 | 34.6 | 30.5 |
| 7d | 1,2-diamino-3-nitro-benzene | 2:1 | lactic | copper-brown | 37.5 | 24.9 | 26.0 |
| 8a | 2-cyanoaniline | 1:2 | none | rose | 57.2 | 35.0 | 24.7 |
| 8b | " | 1:2 | lactic | old rose | 55.9 | 28.3 | 24.2 |
| 8c | " | 2:1 | none | rose | 53.4 | 40.6 | 28.0 |
| 8d | " | 2:1 | lactic | old rose brown | 51.9 | 28.4 | 24.0 |
| 9a | p-phenylenediamine-sulfonic acid | 1:2 | none | bright grey-violet | 49.7 | 13.8 | 1.5 |
| 9b | p-phenylenediamine-sulfonic acid | 1:2 | lactic | dark mahogany | 21.9 | 9.6 | 0.2 |
| 10a | 1-amino-2-naphthalene-4-sulfonic acid | 1:2 | none | salmon | 53.3 | 31.8 | 25.8 |
| 10b | 1-amino-2-naphthalene-4-sulfonic acid | 1:2 | lactic | rose red | 28.2 | 26.6 | 15.3 |
| 11a | 2-(4,5,6-trihydroxy-3-oxo-3H-xanthen-9-yl) sulfonic acid | 1:1 | none | bordeau red | 42.4 | 26.1 | 3.9 |
| 11b | 2-(4,5,6-trihydroxy-3-oxo-3H-xanthen-9-yl) sulfonic acid | 1:1 | lactic | old rose | 41.1 | 27.0 | 13.7 |
| 12a | diaminomaleic acid dinitrile | 1:2 | none | dark-old rose | 35.8 | 19.8 | 3.2 |
| 12b | diaminomaleic acid dinitrile | 1:2 | lactic | rose red | 36.1 | 30.3 | 26.7 |
| 12c | diaminomaleic acid dinitrile | 2:1 | none | dark old rose | 31.0 | 22.2 | 4.2 |
| 12d | diaminomaleic acid dinitrile | 2:1 | lactic | rose red | 34.9 | 28.5 | 21.4 |
| 13a | 2-aminophenol-4-sulfonic acid | 1:2 | none | blond | 66.7 | 15.9 | 27.0 |
| 13b | 2-aminophenol-4-sulfonic acid | 1:2 | lactic | copper-brown | 27.6 | 20.1 | 16.1 |

*Y:Z stands for the amount ratio of the amount of the o-benzoquinone of formula (I) to the amount of the at least one compund of formula (II). Note the color obtained is different depending on whether lactic acid is added or not.

We claim:

1. A non-oxidative dye composition for dyeing keratin fibers, said non-oxidative dye composition comprising an o-benzoquinone compound of formula (I):

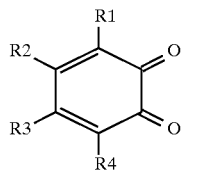
(I)

wherein R1, R2, R3 and R4 are each, independently of each other, hydrogen, chlorine, an alkyl group with from 1 to 5 carbon atoms, an alkoxy group with from 1 to 5 carbon atoms, an alkylenedioxy group with from 1 to 2 carbon atoms or an amino group —$NR^5R^6$, wherein $R^5$ and $R^6$ are each, independently of each other, hydrogen, an alkyl group having from 1 to 6 carbon atoms or an aryl group, and at least one amino- or hydroxy-compound of formula (II)

$$X—A—Y \quad (II),$$

wherein X represents a nitro group, a cyano group or a sulfonate group; Y represents a hydroxy group or an amino group —$NR^aR^b$, wherein $R^a$ and $R^b$ are each, independently of each other, hydrogen or an alkyl group having 1 to 4 carbon atoms, and A represents a substituted or unsubstituted straight chain, cyclic or branched alkyl group having from 1 to 6 carbon atoms or a substituted or unsubstituted aromatic, heterocyclic or carbocyclic group.

2. The composition as defined in claim 1, wherein said at least one amino- or hydroxy-compound of formula (II) is an aniline derivative compound of the formula (IIa)

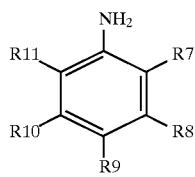
(IIa)

wherein at least one of R7, R8, R9, R10 and R11 represents a nitro group, a cyano group or a sulfonate group, and the remaining of R7 to R11, independently of each other, are each hydrogen, chlorine, a hydroxy group, an amino group, an alkyl group having from 1 to 5 carbon atoms, a hydroxyalkyl group having from 1 to 5 carbon atoms, an alkoxy group having from 1 to 5 carbon atoms, a hydroxyalkoxy group having from 2 to 5 carbon atoms or a carboxyl group;

a phenol derivative compound of the formula (IIb)

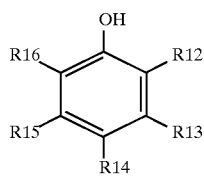
(IIb)

wherein at least one of R12, R13, R14, R15 and R16 represents a nitro group, a cyano group or a sulfonate group, and the remaining of R12 to R16, independently of each other, represent a hydrogen, chlorine, a hydroxy group, a hydroxyalkyl group having from 1 to 5 carbon atoms, an alkoxy group having from 1 to 5 carbon atoms, a hydroxyalkoxy group having from 2 to 5 carbon atoms or a carboxyl group;

a substituted multicenter aromatic isocyclic compound having at least one amino or hydroxy group and at least one nitro group, cyano group or sulfonate group;

a substituted five to six-membered heterocyclic compound with 1 to 3 nitrogen atoms substituted with at least one amino or hydroxy group and at least one nitro group, cyano group or sulfonate group; and/or a substituted open-chain saturated or unsaturated compound having at least two amino group substituents or an amino group and a hydroxy group and at least one nitro group, cyano group or sulfonate group.

3. The composition as defined in claim 1, wherein the at least one amino- or hydroxy-compound of formula (II) is selected from the group consisting of 2-nitroaniline, 3-nitroaniline, 4-nitro-o-phenylenediamine, 2-amino-5-nitrophenol, 1,4-diamino-2-nitrobenzene, 2-amino-3,5-dinitrophenol, picramic acid, 1,2-diamino-3-nitrobenzene, 2-cyanoaniline, diaminomaleic acid dinitrile, 1-amino-2-naphthol-4-sulfonic acid, 2-aminopheno-4-sulfonic acid, 2-(4,5,6-trihydroxy-3-oxo-3H-xanthen-9-yl)benzene sulfonic acid and p-phenylenediamine sulfonic acid.

4. The composition as defined in claim 1, wherein said o-benzoquinone compound of the formula I is selected from the group consisting of 4,5-dimethoxy-1,2-benzoquinone, 4,5-methylenedioxy-1,2-benzoquinone, 4,5-dianilino-1,2-benzoquinone, o-chloranile and 3,5-di-(tert-butyl)-1,2-benzoquinone.

5. The composition as defined in claim 1, containing from 0.02 to 3 percent by weight of the o-benzoquinone compound of the formula I.

6. The composition as defined in claim 1, containing from 0.03 to 6 percent by weight of the at least one amino- or hydroxy-compound of the formula II.

7. The composition as defined in claim 1, having a pH of from 3 to 10.5.

8. The composition as defined in claim 1, comprising a hair dye preparation.

9. The composition as defined in claim 8, wherein said hair dye preparation comprises one component containing said o-benzoquinone compound of the formula I and another component separate from said one component, said another component containing said at least one amino- or hydroxy-compound of the formula II.

10. A non-oxidative process of dyeing human hair comprising the steps of:

a) applying a non-oxidative hair dye composition in an amount sufficient for hair dyeing to the human hair;

b) allowing the non-oxidative hair dye composition to act on the hair for an acting time interval of from 20 to 30 minutes at 20° to 40° C.; and then c) rinsing the hair with water and subsequently drying; wherein the non-oxidative hair dye composition contains an o-benzoquinone compound of formula (I):

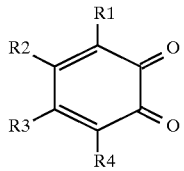 (I)

wherein R1, R2, R3 and R4 are each, independently of each other, hydrogen, chlorine, an alkyl group with from 1 to 5 carbon atoms, an alkoxy group with from 1 to 5 carbon atoms, an alkylenedioxy group with from 1 to 2 carbon atoms or an amino group —$NR^5R^6$, wherein $R^5$ and $R^6$ are each, independently of each other, hydrogen, an alkyl group having from 1 to 6 carbon atoms or an aryl group, and at least one amino- or hydroxy-compound of formula (II)

X—A—Y (II), wherein X represents a nitro group, a cyano group or a sulfonate group; Y represents a hydroxy group or an amino group —$NR^aR^b$, wherein $R^a$ and $R^b$ are each, independently of each other, hydrogen or an alkyl group having 1 to 4 carbon atoms, and A represents a substituted or unsubstituted straight chain, cyclic or branched alkyl group having from 1 to 6 carbon atoms or a substituted or unsubstituted aromatic, heterocyclic or carbocyclic group.

11. A non-oxidative process of dyeing human hair comprising the steps of:
a) applying a first non-oxidative hair dyeing composition component to the hair;
b) within 2 to 5 minutes after the applying of step a), applying a second non-oxidative hair dyeing composition component to the hair;
c) allowing said non-oxidative hair dyeing composition components to act together on the hair for an acting time of from 20 to 40 minutes at at 20° to 40° C.; and then
d) rinsing the hair with water and subsequently drying the hair;

wherein said first hair dyeing composition component includes an o-benzoquinone compound of formula (I):

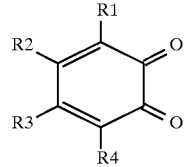 (I)

wherein R1, R2, R3 and R4 are each, independently of each other, hydrogen, chlorine, an alkyl group with from 1 to 5 carbon atoms, an alkoxy group with from 1 to 5 carbon atoms, an alkylenedioxy group with from 1 to 2 carbon atoms or an amino group —$NR^5R^6$, wherein $R^5$ and $R^6$ are each, independently of each other, hydrogen, an alkyl group having from 1 to 6 carbon atoms or an aryl group;

wherein said second hair dyeing composition component is packaged separately from said first hair dyeing composition component and contains at least one amino- or hydroxy-compound of formula (II)

X—A—Y (II)

wherein X represents a nitro group, a cyano group or a sulfonate group; Y represents a hydroxy group or an amino group —$NR^aR^b$, wherein $R^a$ and $R^b$ are each, independently of each other, hydrogen or an alkyl group having 1 to 4 carbon atoms, and A represents a substituted or unsubstituted straight chain, cyclic or branched alkyl group having from 1 to 6 carbon atoms or a substituted or unsubstituted aromatic, heterocyclic or carbocyclic group; and wherein said second hair dyeing composition component does not contain any of said o-benzoquinone compound of the formula (I) and said first hair dyeing composition component does not contain any of said at least one amino- or hydroxy-compound of the formula (II).

* * * * *